United States Patent [19]

Wolf et al.

[11] Patent Number: 4,470,965

[45] Date of Patent: Sep. 11, 1984

[54] CELIPROLOL FOR THE TREATMENT OF GLAUCOMA

[75] Inventors: Peter Wolf, Granite Springs; Morris A. Kesselman, Yonkers, both of N.Y.

[73] Assignee: USV Pharmaceutical Corporation, Tarrytown, N.Y.

[21] Appl. No.: 437,072

[22] Filed: Oct. 27, 1982

[51] Int. Cl.$^3$ .................... A61K 31/17; A61K 31/79
[52] U.S. Cl. ..................................... 424/80; 424/322
[58] Field of Search .................................. 424/322, 80

[56] References Cited

U.S. PATENT DOCUMENTS

| | | | |
|---|---|---|---|
| 3,930,016 | 12/1975 | Berntsson et al. | 424/322 |
| 4,034,009 | 7/1977 | Zölss et al. | 424/322 |
| 4,038,313 | 7/1977 | Wilhelm | 424/322 |
| 4,120,978 | 10/1978 | Wilhelm | 424/322 |
| 4,178,374 | 12/1979 | Sweet | 424/246 |

OTHER PUBLICATIONS

"Glaucoma Update"–Krieglstein et al.–editors–Springer–Verlag–New York–pp. 19-23 (1979)–Langham.
Chem. Abst. 71, 775(w) (1972)–Peori–Giraldi et al.
Arch. Ophthalmol. 95: 601-604 (1977)–Zimmerman et al.
Ophthalmalogica, Basel 184: 198-203 (1982)–Strempel.
Weiner Blinisch Wochenschrift, 90: 350-354 (1978)–Bonelli et al.
Pittner et al.: Celiprolol A Cardioselective Beta–Receptor Blocking Agent, (UL/2006/111, Chemie Linz AG Drug Division, 1982).

Primary Examiner—Douglas W. Robinson

[57] ABSTRACT

An ophthalmic preparation for the treatment of glaucoma by the application to the glaucomatous eye of a celiprolol salt in a pharmaceutically acceptable ophthalmic carrier.

13 Claims, No Drawings

CELIPROLOL FOR THE TREATMENT OF GLAUCOMA

FIELD OF THE INVENTION

This invention relates to compositions and methods for treating intraocular pressure associated with glaucoma. More particularly it relates to the use of celiprolol hydrochloride, as well as selected pharmaceutically acceptable salts thereof, that have been found useful in lowering intraocular pressure.

BACKGROUND OF THE INVENTION

Elevated intraocular pressure is a major risk factor in the onset and development of glaucomatous visual field loss. The higher the level of intraocular pressure, the greater the likelihood of glaucomatous visual field loss and optic nerve damage.

Attempts have been made to lower intraocular pressure in glaucoma by administering to patients certain beta adrenergic blocking agents, commonly known as beta blockers.

In the human body, the beta blockers have several effects. For example, they can reduce the heart rate of an angina patient, which in turn reduces the workload of the heart and thus its need for blood and oxygen. They also tend to decrease the heart's force of contraction, which likewise diminishes the heart's workload. In addition, these drugs reduce the systolic blood pressure which is beneficial to patients with hypertension.

In addition to treating heart ailments, some beta blockers were experimented with for treating other ailments, such as migraine, alcohol and drug withdrawal problems, and glaucoma.

While the use of beta blockers provides valuable benefits to humankind, it also has some undesirable side effects and reactions. Some beta blockers tend to build up in the central nervous system causing fatigue, lethargy, and confusion. Other may cause bronchial spasm and cannot be used in people with bronchial asthma. Still others, while having minimal side effects, fail to produce acceptable results because of their limited potency.

DESCRIPTION OF THE PRIOR ART

Timolol, a non-selective beta-adrenoceptor antagonist, has been shown to lower intraocular pressure in both patients with normal intraocular pressure and in patients with open angle glaucoma. Sold as TIMOPTIC ®, it is the only beta blocker sold in the U.S. for this purpose. Among the adverse reactions reported on the use of timolol is the aggravation or precipitation of certain cardiovascular and pulmonary disorders including bronchospastic disease, sinus bradycardia, cardiogenic shock and cardiac failure. Similarly, atenolol, sotalol, pindolol, oxprenolol, practolol, propranolol, butidrine and metoprolol were reported to have activity in the treatment of glaucoma. However, some of these compounds have been reported to cause pronounced side-effects, for example, methoprolol provokes allergic reactions, oxprenolol may cause corneal epitheliopathy and practolol induces oculomucoculaneous syndrome by immunophathological reactions.

Celiprolol hydrochloride has been shown a selective beta-1-adrenoceptor antagonist having intrinsic sympathomimetic, but no local anesthetic activity.

SUMMARY OF THE INVENTION

It has now been discovered that celiprolol hydrochloride, as well as selected pharmaceutically acceptable salts thereof such as maleate, succinate and the like, when topically applied to the eyes in a pharmaceutically suitable vehicle, such as an ophthalmic solution, is effective in lowering intraocular pressure. Such ophthalmic preparation contain from about 0.01% w/v to about 5.0% w/v, preferably from about 0.03 w/v to about 2.0% w/v of the active ingredient along with inactive ingredients used in the art, such as sodium borate-boric acid, sodium hydroxide to adjust pH, benzalkonium chloride as preservative and water as the vehicle of preference.

It has also been surprisingly discovered that celiprolol hydrochloride, when used according to the present invention, produces bronchodilation following each application and as such possesses significant therapeutic advantage to patients suffering from both glaucoma and respiratory disease.

DETAILED DESCRIPTION OF THE INVENTION

Celiprolol hydrochloride (3-[3-Acetyl-4-[3(tert-butylamino)-2-hydroxy-propoxy]-phenyl]-1, 1-diethylurea hydrochloride) as the free base has the following structure:

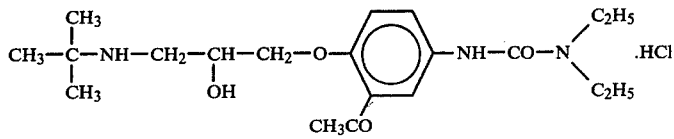

It has a molecular weight of 415.95 having C=57.75%, H=8.24%, N=10.10% O=15.39% and Cl=8.52%

Celiprolol can be prepared according to several pathways described in Austrian Pat. Nos. 334,385 issued to Zoelss, G. et al.; 335,465 to Zoelss, G.; 335,464 to Zoelss, G.; and 335,467 to Zoelss, G. The pathways for preparation of celiprolol according to these patents are as illustrated:

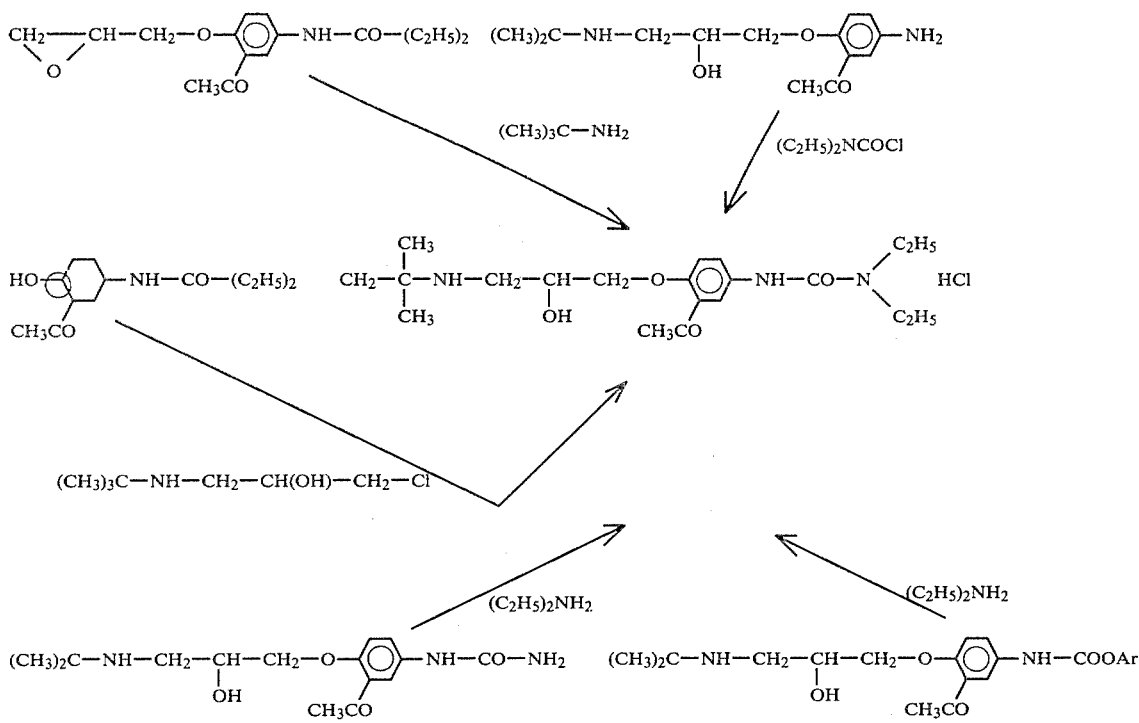

In accordance with the present invention ophthalmic preparations containing celiprolol hydrochloride incorporated in a suitable carrier is applied to the glaucomatous eyes to relieve intraocular pressure. It is to be understood that both the racemic and levorotatory forms of celiprolol hydrochloride are contemplated for use in the present invention, as well as other pharmaceutically acceptable salts of celiprolol, such as maleate, succinate and the like in the range of about 0.01 to about 5% w/v.

The inactive carriers for the active compounds used in the formulations of the present invention include water and ointment bases, such as mineral oil in the range of about 2 to about 10% w/v and white petrolatum in the range of about 90 to about 98% w/v. In preparing the formulations of the present invention, the active compound is solubilized in the carrier. For solubilizing the active compound a co-solvent, in addition to the carrier, may be used. Such co-solvents include glycerin polyethylene glycol fatty acid esters in the range of 1 to 10% w/v, propylene glycol in the range of 1 to 10% w/v, polyethylene glycol in the range of 1 to 15% w/v, polysorbate 20, 60 and 80 in the range of 0.01 to 0.2% w/v and Pluronic F-68 in the range of 0.01 to 2% w/v and mixtures thereof.

To prevent irritation to the eye the isotonicity of the preparation should be in the range of 270 to 330 milliosmoles. Sodium chloride in the range of 0.9±0.1% w/v may be used, if necessary, to adjust the isotonicity.

The ophthalmic preparations of the present invention will have a pH of about 6 to 9 preferably in the range of 7-8. Buffers that may be used to obtain said pH range include alkali metal or alkaline metal earth carbonates, bicarbonates, borates, citrates and tris buffers. More specifically such buffers include 0.01 to 0.2 molar concentrations of boric acid-sodium borate, phosphate buffers, boric acid-sodium bicarbonate, boric acid-sodium citrate, citric acid-sodium phosphate, tris(hydroxymethyl) amino methane-maleic acid and tris(hydroxymethyl)amino methane-HCl.

Other ingredients which may be desirable to use in the ophthalmic preparations of the present invention include viscosity builder agents, preservatives and stabilizers. Examples of these, which may be incorporated into the preparations during the process or after the active compound is solubilized, include the following:

a. preservatives in the range of about 0.001 to about 1.0% w/v;
b. stabilizers in the range of about 0.01 to about 5.0% w/v; and viscosity builders or viscosity agents in the range of about 0.01 to about 2.0% w/v.

More specific examples include:

|  | Range % w/v |
|---|---|
| Preservatives |  |
| Benzalkonium Chloride | 0.004–0.02 |
| Disodium Ethylenediamine Tetraacetate | 0.01–0.20 |
| Thimerosal | 0.001–0.01 |
| Chlorobutanol | 0.5–1.0 |
| Phenylmercuric nitrate | 0.002–0.02 |
| Phenylmercuric acetate | 0.002–0.02 |
| Methyl Paraben | 0.03–0.20 |
| Propyl Paraben | 0.01–0.05 |
| Phenylethyl alcohol | 0.25–0.75 |
| Phenyl mercuric borate | 0.002–0.02 |
| Stabilizers |  |
| Sodium Bisulfite | up to 0.5% |
| Sodium Thiosulfite | up to 0.5% |
| Cysteine | up to 3% |
| Acetyl cysteine | up to 3% |
| B-cyclodextrin | up to 3% |
| Dextran | up to 5% |
| Thiourea | up to 3% |
| Thiosorbitol | up to 3% |
| Monothioglyceryl disodium EDTA | up to 3% |
| Dioctyl Sodium Sulfosuccinate | up to 3% |

|  | Range % w/v |
|---|---|
| Viscosity Agents | |
| Polyvinylpyrrolidone | 0.5–2.0% |
| Polyvinyl alcohol | 0.5–2.0% |
| Methyl cellulose | 0.1–1.0% |
| Hydroxypropyl Methylcellulose | 0.10–1.0% |
| Hydroxyethyl cellulose | 0.10–1.0% |
| Carboxymethyl cellulose | 0.10–1.0% |
| Sodium Carboxymethyl cellulose | 0.01–1.0% |
| Hydroxypropylcellulose | 0.01–1.0% |

In general, the preparations of the present invention may be made and manufactured as illustrated herein:

a., The active drug is dissolved in the aqueous vehicle or thoroughly dispersed in the ointment vehicle by adequate stirring;

b., After dissolution or dispersion of the active drug additional ingredients, such as preservatives, buffer salts, stabilizers and viscosity agents are added and dissolved by further stirring. Sodium chloride is then added, if required, to adjust isotonicity, and the solution is brought to final volume;

c., The product is then sterilized by filtration through a 0.22 micron membrane or alternatively autoclaved at 121°–123° C., or by a combination of both methods;

d., The sterile solution is filled into steile containers and sealed.

The following examples illustrate the present invention without, however, limiting the same thereto.

|  | % w/v |
|---|---|
| EXAMPLE A | |
| Celiprolol | 0.50 |
| Benzalkonium Chloride | 0.01 |
| DiSodium EDTA | 0.10 |
| Purified Water, Q.S | 100.00 |
| EXAMPLE B | |
| Celiprolol | 0.50 |
| Benzalkonium Chloride | 0.01 |
| DiSodium EDTA | 0.10 |
| Boric Acid | 0.215 |
| Sodium Borate, Q.S. to pH 7.4 | |
| Purified Water, Q.S. | 100.00 |
| EXAMPLE C | |
| Celiprolol | 0.125 |
| Thimerosal | 0.002 |
| Tris (Trihydroxyl methyl amino methane | 0.12 |
| Maleic Acid Q.S. to pH 8.3 | |
| Purified Water, Q.S. | 100.00 |
| EXAMPLE D | |
| Celiprolol | 1.00 |
| Benzalkonium Chloride | 0.01 |
| Boric Acid | 1.115 |
| Sodium Borate, Q.S. to pH 7.4 | |
| Polyvinyl Alcohol | 1.4 |
| Purified Water, Q.S. | 100.00 |
| EXAMPLE E | |
| Celiprolol | 3.00 |
| Chlorobutanol | 0.50 |
| Boric Acid | 0.05 |
| Sodium Thiosulfate | 0.30 |
| Sodium Bicarbonate, Q.S. to pH 7.0 | |
| Purified Water, Q.S. | 100.00 |
| EXAMPLE F | |
| Celiprolol | 5.00 |
| Phenyl Mercuric Acetate | 0.02 |
| Methyl Paraben | 0.05 |
| Propyl Paraben | 0.01 |
| Polyvinyl Pyrrolidone | 2.00 |
| Polysorbate 80 | 0.05 |
| Purified Water, Q.S. | 100.00 |

|  | % w/v |
|---|---|
| EXAMPLE G | |
| Celiprolol | 0.50 |
| Benzalkonium Chloride | 0.02 |
| DiSodium EDTA | 0.10 |
| Boric Acid | 0.05 |
| Sodium Borate, Q.S. to pH 6.0 | |
| Polyvinyl Pyrrolidone | 1.50 |
| Hydroxyethyl Cellulose | 0.20 |
| Purified Water, Q.S. | 100.00 |
| EXAMPLE H | |
| Celiprolol | 0.50 |
| Benzalkonium Chloride | 0.005 |
| DiSodium EDTA | 0.05 |
| Boric Acid | 0.215 |
| Sodium Borate, to adjust pH to 7.4 | |
| Polyethylene Glycol 300 | 5.0 |
| Glycerin | 1.0 |
| Sodium Thiosulfate | 0.5 |
| Purified Water, Q.S. | 100.00 |
| EXAMPLE I | |
| Celiprolol | 1.0 |
| Methyl Paraben | 0.05 |
| Propyl Paraben | 0.01 |
| Mineral Oil | 5.0 |
| White Petrolatum, Q.S | 100.00 |
| EXAMPLE J | |
| Celiprolol | 0.5 |
| Chlorobutanol | 0.5 |
| Polyethylene Glycol 400 | 4.0 |
| White Petrolatum, Q.S. | 100.00 |

Illustrative of the benefits obtained in accordance with the present invention, the studies described in the Examples following, were conducted.

EXAMPLE I

This example shows that celiprolol decreases intraocular pressure in dogs and that the decrease is dose-dependent.

Animals, Testing Procedure and Apparatus

Mongrel dogs of either sex weighing between 9 and 16 kg were anesthetized with sodium pentobarbital, 35 mg/kg, i.v. (Ganes Chemical, Pennsville, N.J.). The animals then were intubated with an endotracheal tube (Rusch, size 8–9F, Aristic Surgical, New York, N.Y.) and allowed to breathe spontaneously.

Pulsatile arterial pressure was monitored using a polyethylene catheter (PE 240, Clay-Adams, Parsippany, N.J.) inserted into the right femoral artery and its tips advanced until a distinct dicrotic notch was observed on the arterial pressure tracing. The catheter was connected to a pressure transducer (P23 ID, Statham, Oxnard, CA) and a D.C. driver amplifier (Model 7D, Grass Instruments, Quincy, MA) via a low level D.C. preamplifier (Model 7P1, Grass Instruments). Mean arterial pressure was determined electronically by damping the pulsatile arterial pressure signal. Heart rate was recorded from the output of a tachometer (Model 7PA, Grass Instruments) triggered by the R wave of a Lead II electrocardiogram (EKG-Tachograph Preamplifier, Model 7P4, Grass Instruments). The outputs of arterial pressure and EKG-Tachometer Preamplifier were recorded continuously on an oscillograph (Model 7D, Grass Instruments). Heart rate was measured manually from the tachometer output or calculated from the EKG preamplifier output. Mean arterial pressure was measured manually from the oscillograph tracings. Intraocular pressure was measured using a pneumatonometer (Model 30R, Digilab, Cambridge, MA).

Upon completion of all surgical procedures the animals were allowed to stabilize for 15–30 minutes before pretreatment baseline measurements were taken.

PROTOCOL

Eight mongrel dogs were divided into two groups of four dogs each: the control group and the test group. Two pretreatment baseline measurements of intraocular pressure, mean arterial pressure and heart rate were recorded at −15 and 0 minutes. The mean values of these two readings were used as the pretreatment (0 time) values. The control group was then administered saline topically in a volume of 50 μl instilled into the left eye of each dog at hourly intervals. The test group was administered celiprolol topically in a volume of 50 μl instilled into the left eye of each dog, in ascending concentrations (0.03%, 0.06%, 0.125%, 0.25%, 0.5%), at hourly intervals. Intraocular pressure, mean arterial pressure and heart rate were recorded at 15 minute intervals for 60 minutes post drug or vehicle (saline) administration for each concentration of celiprolol administered and each administration of saline.

Drug Preparation

Celiprolol (RHC 5320-A Lot 2) was dissolved and diluted in normal saline (0.9%, Abbott Laboratories, North Chicago, IL).

The control group received normal saline.

Data Analysis

The absolute change and the percent change from the pretreatment (0 time) values for intraocular pressure, mean arterial pressure and heart rate were expressed as the mean ± S.D. The significance of the difference between the vehicle control group and the celiprolol test group were evaluated using a "t" test for grouped data (as described in SAS T TEST Release 79.5, SAS Institute, Gary, NC 1982). Differences were considered significant if $P<0.05$. In addition, the maximum percent intraocular pressure change for each concentration of celiprolol administered was expressed as the mean ±1 S.D.

Result

Test results are shown in Tables I, II & III.

TABLE I

THE EFFECT OF ASCENDING CONCENTRATIONS OF CELIPROLOL ON INTRAOCULAR PRESSURE (IOP) IN ANESTHETIZED DOGS

| Treatment | N | Baseline[a] Pre-treatment (mm Hg) | Dose Time Minutes Post-treatment | 0.03% | | | | 0.06% | | | | 0.125% | | | |
|---|---|---|---|---|---|---|---|---|---|---|---|---|---|---|---|
| | | | | 15 | 30 | 45 | 60 | 75 | 90 | 105 | 120 | 135 | 150 | 165 | 180 |
| Saline (50 μl of 0.9% NaCl Solution) | 4 | 21 ±2 | Change mm Hg | 0 ±2 | −1 ±3 | −2 ±2 | −3 ±2 | −2 ±3 | −2 ±3 | −4 ±3 | −4 ±2 | −4 ±2 | −4 ±2 | −5 ±1 | −5 ±3 |
| | | | % Change | 2 ±10 | −6 ±13 | −11 ±10 | −14 ±8 | −11 ±13 | −8 ±13 | −17 ±12 | −18 ±11 | −19 ±11 | −21 ±8 | −23 ±7 | −21 ±16 |
| Celiprolol HCl (RHC 5320-A-2 50 μl) | 4 | 30 ±8 | Change mm Hg | −4 ±5 | −5 ±4 | −5 ±3 | −9 ±7 | −10[b] ±5 | −10[b] ±5 | −11[b] ±5 | −10[b] ±2 | −11[b] ±4 | −13[b] ±6 | −11 ±6 | −11 ±6 |
| | | | % Change | −11 ±15 | −15 ±11 | −16 ±9 | −28 ±19 | −33[b] ±10 | −33[b] ±11 | −37[b] ±8 | −34[b] ±5 | −37[b] ±7 | −41[b] ±11 | −36 ±12 | −36 ±16 |

| Treatment | N | Baseline[a] Pre-treatment (mm Hg) | Dose Time Minutes Post-treatment | 0.25% | | | | 0.5% | | | |
|---|---|---|---|---|---|---|---|---|---|---|---|
| | | | | 195 | 210 | 225 | 240 | 255 | 270 | 285 | 300 |
| Saline (50μl of 0.9% NaCl Solution) | 4 | 21 ±2 | Change mm Hg | −5 ±2 | −6 ±2 | −5 ±1 | −5 ±1 | −5 ±4 | −4 ±3 | −5 ±1 | −4 ±1 |
| | | | % Change | −22 ±8 | −27 ±8 | −24 ±5 | −24 ±3 | −23 ±16 | −20 ±13 | −25 ±6 | −20 ±4 |
| Celiprolol HCl (RHC 5320-A-2 50 μl) | 4 | 30 ±8 | Change mm Hg | −13[b] ±6 | −12 ±7 | −14[b] ±6 | −8 ±4 | −12 ±8 | −14[b] ±7 | −14 ±7 | −15[b] ±6 |
| | | | % Change | −43[b] ±10 | −39 ±15 | −47[b] ±8 | −28 ±10 | −41 ±20 | −45[b] ±10 | −44[b] ±12 | −48[b] ±8 |

[a]All values are the mean ± 1 S.D.
[b]$P<0.05$

TABLE II

THE EFFECT OF ASCENDING CONCENTRATIONS OF CELIPROLOL ON MEAN ARTERIAL PRESSURE (MAP) IN ANESTHETIZED DOGS

| Treatment | N | Baseline[a] Pre-treatment (mm Hg) | Dose Time Minutes Post-treatment | 0.03% | | | | 0.06% | | | | 0.1% | | | |
|---|---|---|---|---|---|---|---|---|---|---|---|---|---|---|---|
| | | | | 15 | 30 | 45 | 60 | 75 | 90 | 105 | 120 | 135 | 150 | 165 | 180 |
| Saline (50 μl of 0.9% NaCl Solution) | 4 | 113 ±10 | Change (mm Hg) | 8 ±5 | 6 ±15 | 4 ±11 | 8 ±10 | 9 ±18 | 9 ±8 | 9 ±7 | 10 ±12 | 6 ±15 | 11 ±13 | 8 ±16 | 7 ±17 |
| | | | % Change | 7 ±4 | 5 ±13 | 3 ±10 | 7 ±9 | 8 ±16 | 8 ±7 | 8 ±6 | 8 ±10 | 5 ±13 | 10 ±12 | 7 ±14 | 6 ±15 |
| Celiprolol HCl (RHC 5320-A-2 | 4 | 126 ±15 | Change (mm Hg) | −1 ±10 | 2 ±15 | −3 ±9 | −3 ±8 | −7 ±7 | −8[b] ±10 | −6[b] ±8 | −7 ±9 | −7 ±10 | −3 ±9 | −2 ±5 | 11 ±22 |

TABLE II-continued
THE EFFECT OF ASCENDING CONCENTRATIONS OF CELIPROLOL ON MEAN ARTERIAL PRESSURE (MAP) IN ANESTHETIZED DOGS 50 μl)

| | | | | | | | | | | | |
|---|---|---|---|---|---|---|---|---|---|---|---|
| % Change | 0 ±8 | 2 ±11 | −2 ±7 | −2 ±6 | −5 ±5 | −6[b] ±8 | −5[b] ±6 | −6 ±7 | −6 ±8 | −2 ±7 | −1 ±4 | 10 ±19 |

| Treatment | N | Baseline[a] Pre-treatment (mm Hg) | Dose Time Minutes Post-treatment | 0.3% | | | | 0.5% | | | |
|---|---|---|---|---|---|---|---|---|---|---|---|
| | | | | 195 | 210 | 225 | 240 | 255 | 270 | 285 | 300 |
| Saline (50μl of 0.9% NaCl Solution) | 4 | 113 ±10 | Change (mm Hg) | 12 ±14 | 6 ±10 | 6 ±9 | 7 ±8 | 7 ±6 | 1 ±13 | 3 ±11 | 7 ±11 |
| | | | % Change | 11 ±13 | 5 ±9 | 6 ±8 | 7 ±7 | 6 ±5 | 0 ±11 | 3 ±10 | 6 ±9 |
| Celiprolol HCl (RHC 5320-A-2 50 μl) | 4 | 126 ±15 | Change (mm Hg) | −4 ±10 | −3 ±2 | −4 ±7 | −5 ±16 | −5 ±16 | −4 ±11 | −6 ±14 | −9 ±20 |
| | | | % Change | −4 ±14 | −2 ±9 | −3 ±12 | −5 ±17 | −4 | −3 | −5 | −7 |

[a] All values are the mean ± 1 S.D.
[b] P<0.05

TABLE III
THE EFFECT OF ASCENDING CONCENTRATIONS OF CELIPROLOL ON HEART RATE (BPM) IN ANESTHETIZED DOGS

| Treatment | N | Baseline[a] Pre-treatment (mm Hg) | Dose Time Minutes Post-treatment | 0.03% | | | | 0.06% | | | | 0.1% | | | |
|---|---|---|---|---|---|---|---|---|---|---|---|---|---|---|---|
| | | | | 15 | 30 | 45 | 60 | 75 | 90 | 105 | 120 | 135 | 150 | 165 | 180 |
| Saline (50 μl of 0.9% NaCl Solution) | 4 | 153 ±15 | Change (bpm) | −9 ±9 | −12 ±11 | −17 ±14 | −17 ±18 | −23 ±17 | −18 ±21 | −14 ±19 | −9 ±26 | −24 ±35 | −21 ±31 | −17 ±28 | −23 ±35 |
| | | | % Change | −6 ±5 | −8 ±7 | −11 ±9 | −11 ±12 | −15 ±11 | −12 ±14 | −9 ±13 | −6 ±17 | −16 ±23 | −14 ±21 | −11 ±18 | −15 ±22 |
| Celiprolol HCl (RHC 5320-A-2 50 μl) | 4 | 135 ±14 | Change (bpm) | 0 ±4 | −6 ±9 | −5 ±12 | −5 ±14 | −8 ±14 | −8 ±15 | −9 ±26 | −10 ±16 | −15 ±22 | −5 ±33 | −9 ±33 | 6 ±26 |
| | | | % Change | 0 ±3 | −4 ±7 | −3 ±9 | −4 ±11 | −6 ±11 | −5 ±11 | −7 ±20 | −7 ±12 | −11 ±16 | −3 ±25 | −6 ±24 | 5 ±20 |

| Treatment | N | Baseline[a] Pre-treatment (mm Hg) | Dose Time Minutes Post-treatment | 0.3% | | | | 0.5% | | | |
|---|---|---|---|---|---|---|---|---|---|---|---|
| | | | | 195 | 210 | 225 | 240 | 255 | 270 | 285 | 300 |
| Saline (50μl of 0.9% NaCl Solution) | 4 | 153 ±15 | Change (bpm) | −24 ±35 | −32 ±22 | −26 ±22 | −6 ±20 | −23 ±14 | −30 ±29 | −27 ±14 | −20 ±33 |
| | | | % Change | −16 ±23 | −21 ±15 | −17 ±15 | −4 ±13 | −15 ±10 | −20 ±19 | −18 ±10 | −14 ±22 |
| Celiprolol HCl (RHC 5320-A-2) 50 μl) | 4 | 135 ±14 | Change (bpm) | −3 ±29 | −11 ±17 | −17 ±13 | −17 ±18 | −11 ±25 | −8 ±18 | −18 ±29 | −17 ±35 |
| | | | % Change | −1 ±23 | −7 ±13 | −12 ±8 | −12 ±13 | −7 ±18 | −5 ±13 | −13 ±22 | −12 ±26 |

[a] All values are the mean ± S.D.
[b] P<0.05

Table I shows that celiprolol caused an immediate decrease in intraocular pressure which persisted for the duration of the experiment. The magnitude of the decrease became significantly different (P<0.05) from that of the control group at 75 minutes. The data also indicate that celiprolol causes a dose-dependent decrease in intraocular pressure which reaches a maximum at 0.25% concentration.

Table II shows that the celiprolol group exhibited a small decrease in mean arterial pressure which became significantly different from that of the control at a concentration of 0.06%. Since this decrease in arterial pressure was not dose-dependent, it may be a chance occurrence and not pharmacologically important.

Table III shows that celiprolol had no effect on heart rate at any of the concentrations tested.

EXAMPLE II

This example compares the activity of celiprolol and timolol in dogs on intraocular pressure, systemic arterial pressure and heart rate.

Animals, Testing Procedure and Apparatus

Same as described in Example I.

Drug Preparation

Celiprolol and saline were used as shown in Example I. Timolol (TIMOPTIC®, 0.5%, Merck Sharp and Dohme, West Point, PA) was used.

PROTOCOL

Mongrel dogs were screened for intraocular pressure and only dogs that had intraocular pressures between 23 mmHg and 28 mmHg were chosen in this study.

Twelve mongrel dogs which met the above-described criterion were subdivided into three groups of four dogs each. The control group had a mean intraocular pressure of 25.3±0.6 mmHg; the celiprolol, or test, group had a mean intraocular pressure of 25.6±0.6 mmHg; and the timolol group, with which the celiprolol group was compared, had a mean intraocular pressure of 25.2±1.6 mmHg.

Two pretreatment baseline measurements of intraocular pressure, mean arterial pressure and heart rate were recorded at 31 15 and 0 minutes for each groups. The mean values of these two readings were used as pretreatment (0 time) values 0.5% celiprolol in a volume of 50 μl was then administered into the left eye of each dog in the test or celiprolol group; 0.5% timolol in a volume of 50 μl was administered into the left eye of each dog in the timolol group; and 50 μl of saline was administered into the left eye of each dog in the control group.

Intraocular pressure, mean arterial pressure and heart rate measurements were made at various intervals for five hours respectively for post drug or saline administration.

Data Analysis

Same as in Example 1.

Results

Test results are shown in Tables IV, V and VI Table IV shows that at equal doses both celiprolol and timolol were effective in decreasing intraocular pressure in anesthetized dogs. Celiprolol, however, caused a significant change from control of the one hour post drug administration which persisted for the duration of the study, while timolol attained a significant difference from the control only after 180 minutes post drug administration, which from thereon also persisted for the duration of the experiment.

Table V shows that neither celiprolol nor timolol had any significant effect on mean arterial pressure.

Table VI shows that celiprolol seems to have no effect on heart rate whereas timolol at least for the first two hours has a tendency to decrease heart rate.

TABLE IV

THE EFFECT OF TOPICALLY ADMINISTERED CELIPROLOL AND TIMOLOL ON INTRAOCULAR PRESSURE (IOP) IN ANESTHETIZED DOGS

| Treatment | N | Baseline[a] Pre-treatment (mm Hg) | | 15 | 30 | 45 | 60 | 90 | 120 | 150 | 180 | 210 | 240 | 270 | 300 |
|---|---|---|---|---|---|---|---|---|---|---|---|---|---|---|---|
| Saline 50 μl (0.9% NaCl Solution) | 4 | 25 ±1 | Change (mm Hg) | −1 ±3 | −2 ±5 | 0 ±4 | 0 ±3 | 0 ±2 | −2 ±3 | −1 ±5 | 0 ±4 | 0 ±4 | 1 ±5 | 1 ±2 | −2 ±2 |
| | | | % Change | −5 ±11 | −6 ±21 | 1 ±16 | −1 ±11 | −1 ±9 | −8 ±10 | −5 ±19 | −1 ±16 | −1 ±15 | −4 ±19 | 3 ±7 | −6 ±10 |
| Celiprolol HCl (RHC 5320-A) 50 μl 0.5% Solution | 4 | 25 ±1 | Change (mm Hg) | −4 ±0 | −3 ±1 | −4 ±2 | −6[b] ±2 | −5[b] ±2 | −6[b] ±2 | −8[b] ±3 | −8[b] ±2 | −9[b] ±2 | −9[b] ±2 | −10[b] ±1 | −10[b] ±2 |
| | | | % Change | −15 ±0 | −11 ±5 | −16 ±10 | −23[b] ±6 | −21[b] ±6 | −25[b] ±8 | −33[b] ±11 | −31[b] ±7 | −37[b] ±9 | −36[b] ±7 | −38[b] ±5 | −41[b] ±8 |
| Timolol Maleate (Timoptic) 50 μl of 0.5 Solution | 4 | 25 ±2 | Change (mm Hg) | −1 ±3 | −3 ±4 | −5 ±5 | −4 ±7 | −6 ±4 | −7 ±4 | −8 ±5 | −8[b] ±3 | −8[b] ±2 | −8[b] ±2 | −7[b] ±5 | −8 ±5 |
| | | | % Change | −1 ±13 | −13 ±17 | −20 ±20 | −15 ±28 | −22 ±15 | −25 ±16 | −32 ±20 | −31[b] ±11 | −30[b] ±6 | −31[b] ±6 | −27[b] ±18 | −30[b] ±16 |

[a]All values are expressed as the mean ± 1 S.D.
[b]P<0.05

TABLE V

THE EFFECT OF TOPICALLY ADMINISTERED CELIPROLOL AND TIMOLOL ON MEAN ARTERIAL PRESSURE (MAP) IN ANESTHETIZED DOGS

| Treatment | N | Baseline[a] Pre-treatment (mm Hg) | | 15 | 30 | 45 | 60 | 90 | 120 | 150 | 180 | 210 | 240 | 270 | 300 |
|---|---|---|---|---|---|---|---|---|---|---|---|---|---|---|---|
| Saline 50 μl (0.9% NaCl Solution) | 4 | 120 ±13 | Change (mm Hg) | 4 ±3 | 3 ±8 | 3 ±4 | 2 ±6 | 2 ±5 | −2 ±11 | 2 ±10 | 5 ±5 | 5 ±13 | 2 ±11 | 0 ±8 | 5 ±9 |
| | | | % Change | 3 ±2 | 2 ±6 | 3 ±3 | 2 ±5 | 2 ±5 | −2 ±10 | 2 ±9 | 4 ±5 | 4 ±12 | 2 ±10 | 0 ±7 | 4 ±8 |
| Celiprolol HCl (RHC 5320-A) 50 μl 0.5% Solution | 4 | 113 ±8 | Change (mm Hg) | 2 ±2 | 4 ±4 | 4 ±8 | 5 ±8 | 5 ±7 | 10 ±7 | 0 ±12 | 3 ±8 | 5 ±5 | 3 ±8 | −2 ±8 | −1 ±11 |
| | | | % Change | 2 ±2 | 4 ±3 | 3 ±6 | 4 ±7 | 5 ±6 | 9 ±7 | 0 ±10 | 3 ±7 | 4 ±5 | 2 ±6 | −2 ±7 | −1 ±9 |
| Timolol Maleate (Timoptic) 59 μl 0.5% Solution | 4 | 106 ±6 | Change (mm Hg) | −2 ±6 | −4 ±6 | −3 ±7 | −5 ±7 | −3 ±7 | −8 ±26 | −5 ±16 | −3 ±9 | −1 ±8 | −6 ±5 | −2 ±9 | −5 ±6 |
| | | | % | −2 | −4 | −3 | −4 | −3 | −7 | −4 | −3 | −1 | −6 | −1 | −4 |

TABLE V-continued
THE EFFECT OF TOPICALLY ADMINISTERED CELIPROLOL AND TIMOLOL ON MEAN ARTERIAL PRESSURE (MAP) IN ANESTHETIZED DOGS

| Treatment | N | Baseline[a] Pre-treatment (mm Hg) | | 15 | 30 | 45 | 60 | 90 | 120 | 150 | 180 | 210 | 240 | 270 | 300 |
|---|---|---|---|---|---|---|---|---|---|---|---|---|---|---|---|
| | | | Change | ±6 | ±6 | ±6 | ±6 | ±7 | ±25 | ±15 | ±9 | ±8 | ±4 | ±9 | ±6 |

[a] All values are expressed as the mean ± 1 S.D.
[b] $P < 0.05$

TABLE VI
THE EFFECT OF TOPICALLY ADMINISTERED CELIPROLOL AND TIMOLOL ON HEART RATE (BMP IN ANESTHETIZED DOGS

| Treatment | N | Baseline[a] Pre-treatment (mm Hg) | | 15 | 30 | 45 | 60 | 90 | 120 | 150 | 180 | 210 | 240 | 270 | 300 |
|---|---|---|---|---|---|---|---|---|---|---|---|---|---|---|---|
| Saline 50 μl 0.9% NaCl Solution | 4 | 122 ±24 | Change (bpm) | 6 ±11 | 5 ±20 | 3 ±15 | 0 ±20 | 0 ±14 | 8 ±10 | −9 ±26 | −3 ±20 | −5 ±25 | −13 ±31 | −13 ±30 | −12 ±18 |
| | | | % | 6 | 3 | 3 | 1 | 0 | 7 | −7 | −1 | −3 | −9 | −10 −10 | |
| | | | Change | ±11 | ±15 | ±12 | ±16 | ±11 | ±9 | ±18 | ±15 | ±19 | ±23 | ±21 | ±14 |
| Celiprolol HCl (RHC 5320-A) 50 μl 0.5% Solution | 4 | 137 ±21 | Change (bpm) | −5 ±6 | −10 ±10 | −8 +18 | −5 ±15 | −8 ±11 | −5 ±18 | −21 ±20 | −11 ±16 | −11 ±9 | −18 ±23 | −18 ±21 | −28 ±10 |
| | | | % | −4 | −8 | −6 | −4 | −5 | −5 | −17 | −9 | −9 | −14 | −14 | −22 |
| | | | Change | ±4 | ±9 | ±15 | −11 | ±9 | ±14 | ±15 | ±12 | ±8 | ±17 | ±16 | ±10 |
| Timolol Maleate (Timoptic) 50 μl 0.5% Solution | 4 | 119 ±22 | Change (bpm) | −12 ±11 | −19 ±11 | −25[b] ±17 | −28 ±18 | −25 ±25 | −17 ±41 | −19 ±38 | −28 ±33 | −23 ±37 | −26 ±32 | −26 ±48 | −29 ±26 |
| | | | % | −9 | −15 | −19[b] | −22 | −18 | −10 | −11 | −19 | −15 | −18 | −16 | −22 |
| | | | Change | ±9 | ±8 | ±12 | ±13 | ±21 | ±39 | ±35 | ±29 | ±33 | ±29 | ±46 | ±22 |

[a] All values are expressed as the mean ± 1 S.D.
[b] $P < 0.05$

In asthmatic patients airway constriction has been reported as the result of the use of certain β-blockers. The present invention, utilizing celiprolol, provides for the treatment of glaucoma without having the deleterious side effect of airway constriction associated with certain β-blockers, such as atenolol, metoprolol, propanolol and timolol. Example III describes the comparative study conducted on celiprolol with three other beta blocking agents for effects on bronchomotor tone in mechanically ventillated cats infused with serotonin.

EXAMPLE III

Method

Male cats (3–5 kg) were anesthetized with pentobarbital sodium, 35 mg/kg i.p. Maintenance anesthetic was administered intravenously as needed. The trachea of each cat was cannulated and a pneumotachograph placed on-line for monitoring air flow. A differential pressure tranducer placed between the tracheal cannula and a cannula in the pleural cavity was used to monitor transpulmonary pressure. Electronic signals proportional to air flow and transpulmonary pressure were converted by an on-line analog computer to values of pulmonary (airway) resistance, $R_{AW}$, for each breath. Cannulae were inserted into the right femoral artery and both femoral veins. The arterial cannula was used for monitoring blood pressure and heart rate. In addition, it allowed for withdrawal of arterial blood samples for assessment of $PO_2$, $PCO_2$ and pH, as a means of confirming the adequacy of ventilation. The animal was paralyzed with gallamine triethiodide (Flaxedil, 20 mg i.v.) and mechanically ventilated.

In order to test for bronchodilator activity, it was necessary to increase the normally low bronchomotor tone of the cat. This increase was induced by a constant i.v. infusion of serotonin (5-HT), approximately 20 μg/kg/min. During this steady state bronchoconstriction, each animal received three or four increasing bolus doses of a single beta blocker, either atenolol (1–10 mg/kg i.v.), celiprolol hydrochloride (1–10 mg/kv i.v. or 10–100 mg/kg i.d.), metoprolol tartrate (1–10mg/kg i.v.) or timolol maleate (0.03–3 mg/kg i.v.). Doses are expressed as the free bases. All drugs were dissolved in 0.9% saline, except timolol, which was used in the form of Timoptic® ophthalmic solution suitably diluted with saline. In experiments in which celiprolol was given intraduodenally, needle-tipped cannulae were surgically inserted into the duodena of cats fasted for 16 hours.

Drug-induced changes in bronchomotor tone, averaged over 6-second intervals, were calculated as percent changes in $R_{AW}$ from the steady state values established by serotonin infusion. Mean ± standard deviation were calculated for experiments in which n=3. Data for one celiprolol dose, 10 mg/kg i.d., were calculated using n=2. Statistical analysis was carried out with the t-test for paired data.

RESULTS

The results are shown in Table VII wherein $R_{AW}$ = % change in airway resistance; HR = heart rate—breaths/minute; i.v. = intravenous; i.d. = intraduodenal.

TABLE VII

| COMPOUND | mg/kg i.v. | HR | RAW |
|---|---|---|---|
| ATENOLOL | 1 | −8 ± 5 | 23 ± 12 |
| " | 3 | −6 ± 3 | 14 ± 5 |
| " | 10 | −6 ± 2 | 48 ± 34 |

TABLE VII-continued

| COMPOUND | mg/kg i.v. | HR | RAW |
|---|---|---|---|
| METROPROLOL | 1 | −17 ± 11 | 50 ± 23 |
| " | 3 | −25 ± 19 | 43 ± 21 |
| " | 10 | −94 ± 86 | 105 ± 37 |
| TIMOLOL | 0.3 | −8 ± 8 | 11 ± 9 |
| " | 1 | −8 ± 1 | 18 ± 51 |
| CELIPROLOL | 1 | −1 ± 10 | −62 ± 10 |
| " | 3 | −9 ± 4 | −65 ± 10 |
| " | 10 | −27 ± 7 | −70 ± 14 |

As shown in the table, intravenous administration of atenolol, metoprolol and timolol caused dose-dependent bronchoconstriction, i.e. increased $R_{AW}$. Bronchoconstriction has increased to 48% with atenolol, to 105% with metoprolol and to 49% with timolol. In contrast, celiprolol produced bronchodilation, i.e. $R_{AW}$ decreased to −70%.

The duration of the bronchodilator effect of celiprolol was about 14 minutes at 1 and 3 mg/kg. The effect of 10 mg/kg lasted for more than 40 minutes.

EXAMPLE IV

The procedure in this example generally follows the procedure used in Example III, except that the test compounds of celiprolol and timolol were administered topically as follows. 50 μl of test solution was instilled into the eyes of anesthetized cats whose airway resistance, $R_{AW}$, had been increased by infusion of serotonin. Three doses of timolol (5 mg/ml) further increased $R_{AW}$ by 20 to 35%. Similar doses of celiprolol decreased $R_{AW}$ by 21 to 23%.

EXAMPLE V

This procedure in this example generally follows the procedure used in Example III, except that celiprolol was administered to cats intraduodenally. Tested in the range of 10–100 mg/kg, celiprolol reduced $R_{AW}$ by 29 to 41%.

Having described the invention, those skilled in the art will know modifications within the spirit thereof, and the invention is to be limited only within the scope of the appended claims.

What is claimed is:

1. A method of treating glaucoma comprising topically applying a therapeutic effective amount of celiprolol hydrochloride or pharmaceutically acceptacle salts thereof.

2. The method of claim 1 wherein said therapeutic agent is present from about 0.01 to about 5.0% w/v concentrations in a pharmaceutically acceptable carrier.

3. The method of claim 1 wherein said pharmaceutically acceptable carrier is a water base.

4. The method of claim 1 wherein said pharmaceutically acceptable carrier is an ointment base.

5. The method of claim 1 wherein the isotonicity of said preparation is within the range of 270 to 330 milliosmoles.

6. The method of claim 1 wherein the pH of said preparation is in the range of 6 to 9.0.

7. The method of claim 1 further comprising a buffer, a tonicity agent, a preservative, a stabilizer, a co-solvent and a viscosity agent.

8. An ophthalmic preparation for the treatment of glaucoma comprising:
   a. celiprolol hydrochloride or pharmaceutically acceptable salts thereof 0.03–2.0% w/v;
   b. 1 to 10% w/v of a co-solvent selected from the group consisting of glycerin, propylene glycol, or polyethylene glycol;
   c. 0.01 to 2.0% w/v of a viscosity agent selected from the group consisting of polyvinylpyrrolidone, polyvinyl alcohol, methyl cellulose, hydroxypropyl methylcellulose, hydroxyethyl cellulose and carboxymethylcellulose, sodium carboxymethylcellulose or hydroxypropylcellulose
   d. 0.01 to 5.0% w/v of a stabilizer selected from the group consisting of sodium bisulfite, sodium thiosulfite, cysteine, acetyl cysteine, β-cyclodextrin, dextran and thiourea, thio-sorbitol, morothioglycerol, sodium EDTA, or sodium sulfosuccinate;
   e. a 0.01 to 0.20 molar buffer selected from the group consisting of boric acid-sodium borate, phosphate buffer, boric acid-sodium bicarbonate, boric acid-sodium citrate, citric acid-sodium phosphate, tris(hydroxymethyl) amino methanemaleic acid and tris(hydroxymethyl) amino methane-HCl;
   f. 0.001 to 1.0% w/v of a preservative selected from the group consisting of benzalkonium chloride, disodium ethylenediamine tetraacetate, thimerosal, chlorobutanol, phenylmercuric nitrate, phenylmercuric acetate, methyl paraben, propyl paraben, phenyl mercuric borate or phenylethyl alcohol; and
   g. water Q.S. to 100%.

9. An ophthalmic preparation for the treatment of glaucoma comprising about 0.03 to about 0.5% w/v of celiprolol hydrochloride and pharmaceutically acceptable salts thereof in a pharmaceutically acceptable carrier which comprises in % w/v:
   boric acid—sodium borate—0.03
   benzalkonium chloride—0.01
   disodium ethylenediamine tetraacetate—0.1
   sodium thiosulfite—0.3
   polyvinylpyrrolidone—1.5
   hydroxyethyl cellulose—0.1
   polysorbate 80—0.01
   water q.s. to 100, and having an isotonicity range of 270 to 330 milliosmoles.

10. An ophthalmic preparation for the treatment of glaucoma comprising:
    a. 0.01–5.00% w/v celiprolol hydrochloride or pharmaceutically acceptable salts thereof:
    b. 0.01 to 0.20 molar buffer selected from the group consisting of boric acid-sodium borate, phosphate buffer, boric acid-sodium bicarbonate, boric-acid-sodium citrate, citric acid-sodium phosphate, tris(hydroxymethyl) amino methanemaleic acid and tris(hydroxymethyl) amino methane-HCl;
    c. 0.001 to 1.0% w/v a preservative selected from the group consisting of benzalkonium chloride, disodium ethylenediamine tetraacetate, thimerosal, chlorobutanol, phenylmercuric nitrate, phenylmercuric acetate, methyl paraben, propyl paraben, phenyl mercuric borate or phenylethyl alcohol; and
    d. water Q.S. to 100%.

11. The ophthalmic preparation of claim 10 further comprising a tonicity agent.

12. The ophthalmic preparation of claim 11 wherein the isotonicity of said preparation is within the range of 270 to 330 milliosmoles.

13. A method for the treatment of glaucoma comprising applying to the eye of a patient in need of such treatment an effective amount for lowering intraocular pressure therein a composition of claim 10.

* * * * *